US009125687B2

United States Patent
Yoon et al.

(10) Patent No.: US 9,125,687 B2
(45) Date of Patent: Sep. 8, 2015

(54) AMNIOTIC FLUID COLLECTOR

(75) Inventors: Bo Hyun Yoon, Seoul (KR); Chan Wook Park, Seoul (KR); Seung Mi Lee, Seoul (KR); Joong Shin Park, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 174 days.

(21) Appl. No.: 13/639,600

(22) PCT Filed: Apr. 5, 2011

(86) PCT No.: PCT/KR2011/002348
§ 371 (c)(1),
(2), (4) Date: Oct. 5, 2012

(87) PCT Pub. No.: WO2011/126258
PCT Pub. Date: Oct. 13, 2011

(65) Prior Publication Data
US 2013/0030325 A1   Jan. 31, 2013

(30) Foreign Application Priority Data
Apr. 6, 2010   (KR) .................. 10-2010-0031404

(51) Int. Cl.
*A61B 17/42*   (2006.01)
*A61B 10/00*   (2006.01)
*A61M 1/00*   (2006.01)

(52) U.S. Cl.
CPC ......... *A61B 17/4208* (2013.01); *A61B 10/0048* (2013.01); *A61B 10/0045* (2013.01); *A61M 1/0009* (2013.01)

(58) Field of Classification Search
CPC ........... A61B 10/0045; A61B 10/0048; A61B 17/4208; A61M 1/009; A61M 3/0295
USPC ......... 600/582, 580, 581; 604/328, 96, 96.01, 604/101.01; 606/125
See application file for complete search history.

(56) References Cited

U.S. PATENT DOCUMENTS 4,693,704 A * 9/1987 Ogita .............................. 604/515
4,976,692 A * 12/1990 Atad ........................ 604/101.03
(Continued)

FOREIGN PATENT DOCUMENTS

| EP | 0719571 | 12/1995 |
|---|---|---|
| JP | 11000336 | 1/1999 |
| JP | 2005305094 | 11/2005 |

OTHER PUBLICATIONS

Barnhart, Kurt T. et al. "Baseline dimensions of the human vagina." 2006. Human Reproduction, vol. 21, No. 6. pp. 1618-1622.*
(Continued)

*Primary Examiner* — Devin Henson
(74) *Attorney, Agent, or Firm* — Lucas & Mercanti, LLP

(57) ABSTRACT

According to the present invention, an amniotic fluid collector is configured so as to be inserted and positioned inside the vagina of a birthing mother in order to collect amniotic fluid from the womb of the birthing mother. In particular, the amniotic fluid collector of the present invention comprises: a receiving member, in the side of which an opening is defined, which is inserted into the vagina of the birthing mother and which has a receptacle defined therein for receiving the amniotic fluid; and a positioning portion for positioning the receiving member inside the vagina. Thus, the effects of alleviating pain and psychological anxiety of a birthing mother and eliminating the danger of the occurrence of complications can be achieved, as well as those of easily and smoothly collecting amniotic fluid from the womb of the birthing mother.

8 Claims, 9 Drawing Sheets

(56) References Cited

U.S. PATENT DOCUMENTS

| | | | | |
|---|---|---|---|---|
| 5,104,377 | A | * | 4/1992 | Levine ............... 604/101.05 |
| 5,338,297 | A | * | 8/1994 | Kocur et al. ............ 604/103.03 |
| 2006/0058831 | A1 | * | 3/2006 | Atad ...................... 606/193 |
| 2009/0281456 | A1 | | 11/2009 | Park et al. |

OTHER PUBLICATIONS

Brook, I. et al. "Ultrasonography in the diagnosis of cervical incompetence in pregnancy—A new diagnostic approach." Jun. 1981. British Journal of Obstetrics and Gynaecology, vol. 88. pp. 640-643.*

* cited by examiner

AMNIOTIC FLUID COLLECTOR

CROSS-REFERENCE TO RELATED APPLICATIONS

This patent application is a U.S. national phase under 35 U.S.C. 371 of PCT/KR2011/002348 filed on Apr. 5, 2011, which claims the benefit of priority from Korean Patent Application No. 10-2010-0031404, filed on Apr. 6, 2010, the contents of each of which are incorporated herein by reference in its entirety.

BACKGROUND OF THE INVENTION

1. Field of the Invention

The present invention relates to an amniotic fluid collector, and more particularly, to an amniotic fluid collector capable of conveniently and efficiently collecting amniotic fluid from the uterus of a pregnant woman, while eliminating pains or psychological anxiety of the pregnant woman, and also eliminating risk of complications of the pregnant woman.

2. Description of the Related Art

Generally, in the uterus of a pregnant woman, there are a fetus and amniotic fluid. Also, along the pregnancy, various medical examinations are performed with respect to a pregnant woman and fetus.

Particularly, amniotic fluid is generally collected from the uterus of a pregnant woman to check whether there are a sign of premature labor, an infection in amniotic fluid, an inflammation and infection in a fetus, a damage of a fetus, a fetal maturity, fetal diseases, and fetal deformities and also to examine ingredients of amniotic fluid, by directly injecting a syringe for collecting amniotic fluid into the abdomen of a pregnant woman, and this is performed inevitably using the way as described above and also performed when disease names are not clearly identified.

Also, sputter coating is a method in which electrons generated by applying a negative bias to a sputter gun in a vacuum system disassociate an inactive gas and generate plasma and ion particles with high energy generated thereby collide with a surface of a target where ion particles are to be evaporated to and exchange kinetic energy in such a way that atoms or molecules bounce out of the surface and are absorbed onto a substrate. The sputter coating has a problem in which collision of particles with energy generates defects and forms local trap sites, thereby causing a structural organic distortion of an organic film. Also, the collision elevates a temperature of the surface and deteriorates properties of an organic layer.

However, when injecting a syringe, a pregnant woman may feel the pain and restlessness and there is a risk of developing complications and even medical accidents due to the examination.

SUMMARY OF THE INVENTION

To solve the problems as described above, the present invention provides an amniotic fluid collector capable of conveniently and efficiently collecting amniotic fluid from the uterus of a pregnant woman, without causing pains or psychological discomforts, and risks of complications of the pregnant woman.

To achieve the goal as described above, an amniotic fluid collector according to a preferable embodiment of the present invention is configured to be inserted to and positioned in the vagina of a pregnant woman to collect amniotic fluid from the uterus of the pregnant woman.

To be specific, the amniotic fluid collector may include a receiving member comprising an aperture formed on one side in a direction of insertion into the vagina of the pregnant woman and a receiving compartment formed therein to receive the amniotic fluid, and a positioning portion for positioning the receiving member inside the vagina.

The receiving member may preferably be formed from a material comprising natural rubber, urethane or plastic, which is harmless to a human body.

The positioning portion may preferably include an expandable member which surrounds the receiving member and which is expandable upon injection of an injection material therein, to securely urge against an inner surface of the vagina and thereby secure the receiving member in position.

The expandable member may preferably be formed from a material comprising silicone with elasticity and flexibility.

The injection material may preferably include air or water.

The positioning portion may preferably additionally include a supplying tube having one end inserted into the expandable member for fluid-connection and the other end through which the injection material is supplied.

In one embodiment, the amniotic fluid collector may additionally include a grip tube connected to the receiving member to cause the aperture of the receiving member, inserted into the vagina, to be brought into a close contact with a top of the vagina and also to exert a withdrawal force to remove the receiving member from the vagina. The supplying tube may be preferably formed in such a way that the one end thereof, inserted in the expandable member, is extended to be inserted into the grip tube, and the other end is disposed outside through the grip tube.

The grip tube may be preferably formed from a material comprising natural rubber, urethane or plastic, which has no harm to a human body.

In one embodiment, the amniotic fluid collector may additionally include a guide member with hardness to be inserted in the grip tube in order to apply an insertion force to insert the receiving member into the vagina.

The guide member may be preferably formed from a material comprising iron.

Because the amniotic fluid collector according to the present invention includes a receiving member having a receiving compartment, and a positioning portion for positioning the receiving member, it is possible to collect amniotic fluid from the uterus of the pregnant woman conveniently and efficiently, without causing pains, restlessness, or a risk of complications of a pregnant woman.

DETAILED DESCRIPTION OF EXEMPLARY EMBODIMENTS

Figure 1:
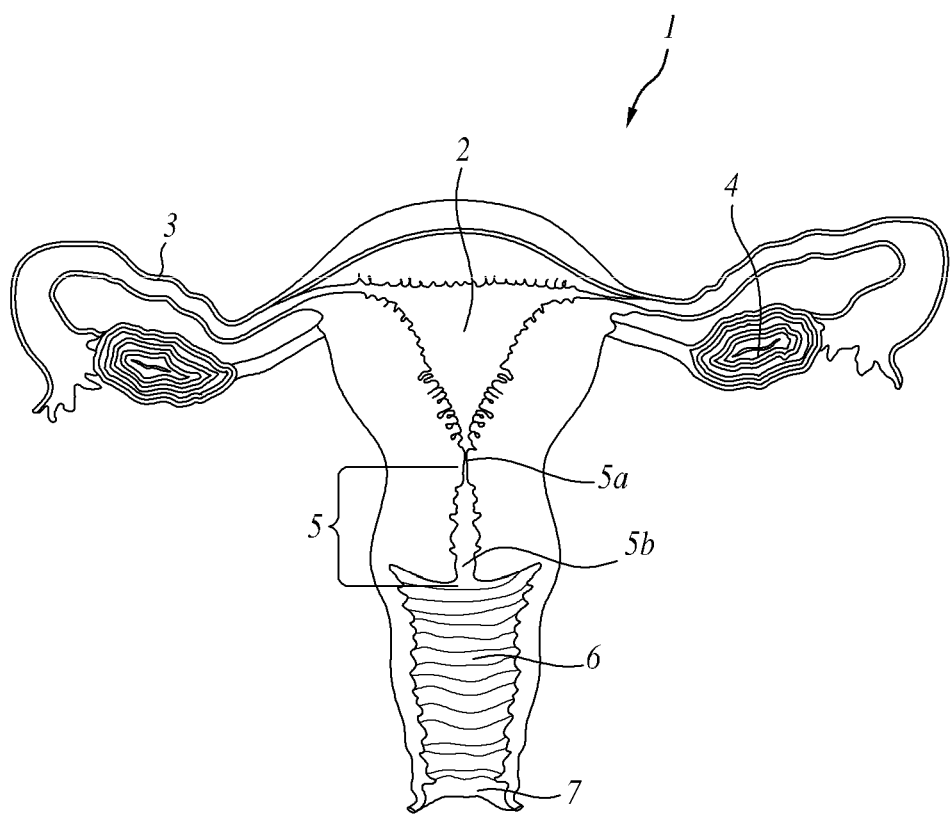
FIG. 1 is a view illustrating an interior of female reproductive organs.

An amniotic fluid collector according to an embodiment of the present invention is configured to be inserted into vagina of a pregnant woman and positioned therein to collect amniotic fluid from the uterus of the pregnant woman.

An amniotic fluid collector according to an embodiment of the present invention is configured to be inserted into vagina of a pregnant woman and positioned therein to collect amniotic fluid from the uterus of the pregnant woman.

The reproductive organs 1 of a woman include an external reproductive organ including a vaginal entrance 7, and internal reproductive organs including vagina 6, uterus 2, fallopian tubes 3 and ovaries 4.

The ovaries 4 are where ovum is produced and female hormones are released. The ovulation occurs in the ovaries 4 in which a matured ovum is released.

In detail, as a result of ovulating alternately, eggs are released from both ovaries 4 once in two months, that is, an egg comes out once in a month.

Also, as an inner wall of the uterus 2 becomes thicker in the ovulation and if fertilized eggs are not implanted, thicker tissues thereof are ruptured, menstruation commences.

The menstruation generally occurs once in a month. However, the menstrual cycle may not be regular for one or two years after the first menarche, or even before a marriage.

The ovaries 4 are each located on both upper sides behind the uterus 2 and act like testicles of a male. That is, the ovaries 4 generate, grow, and release eggs and release female hormones.

The size of the ovaries 4 varies depending on age. The ovaries 4 of an adult have the same size as that of an apricot, which becomes notably reduced to a size little greater than a small bean after menopause.

On the other hand, the uterus 2 is a muscular system having a thick membrane capable of well swelling to hold therein a fetus till the last phase of pregnancy.

The uterus 2 is in the shape of a pear with varying sizes.

Mainly, the uterus 2 allows menstruation to occur, allows a fertilized egg to be implanted in the inner wall of the uterus 2, maintains pregnancy, and allows a fetus to grow from early stages of pregnancy to a labor.

Additionally, the inside of the uterus 2 is hollow, with a bladder located in front, and rectum located at the back.

The vagina 6 is a muscular tube extended from vulva to the uterus 2, and there are urethra and bladder in front of the vagina 6 while there is rectum at the back.

An upper portion of the vagina 6 is connected to cervix 5. The vagina 6 has a length of about 2 to 7 cm, and is both an eliminatory organ, through which secretions and menstrual blood of the uterus 2 are discharged, and a sex organ.

In addition, the vagina 6 plays a role of a parturient canal through which a baby passes in a labor. A vaginal sac that is an inner space of the vagina 6 is always moist due to secretions discharged from a mucous membrane of the uterus 2 and an inside entrance 5a and an outside entrance 5b of the cervix 5 and mucus discharged from the vaginal sac.

In this case, vaginal mucus maintains acidity, prevents invasion of germs, and restrains propagation of general bacteria.

On the other hand, labia minora (not illustrated) are located inside labium majus (not illustrated), and are covered with adipose tissues and a mucous membrane, have no hair follicles, and become red when sexually excited. A top thereof is covered with clitoric epidermis.

Figure 5:
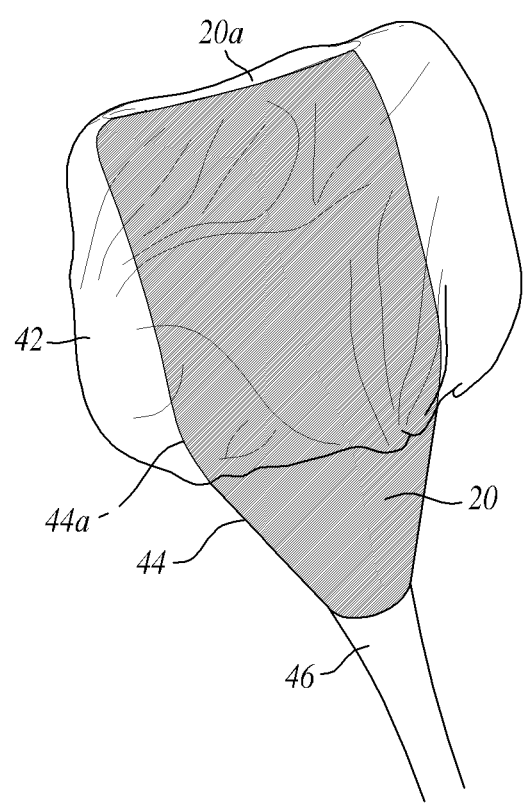
FIG. 5 is an enlarged view of a portion A of FIG. 2.

With reference to FIG. 5, an amniotic fluid collector according to an embodiment of the present invention, which is capable of being inserted into a vagina in female reproductive organs as described above and collecting amniotic fluid therefrom, will be explained.

Figure 2:
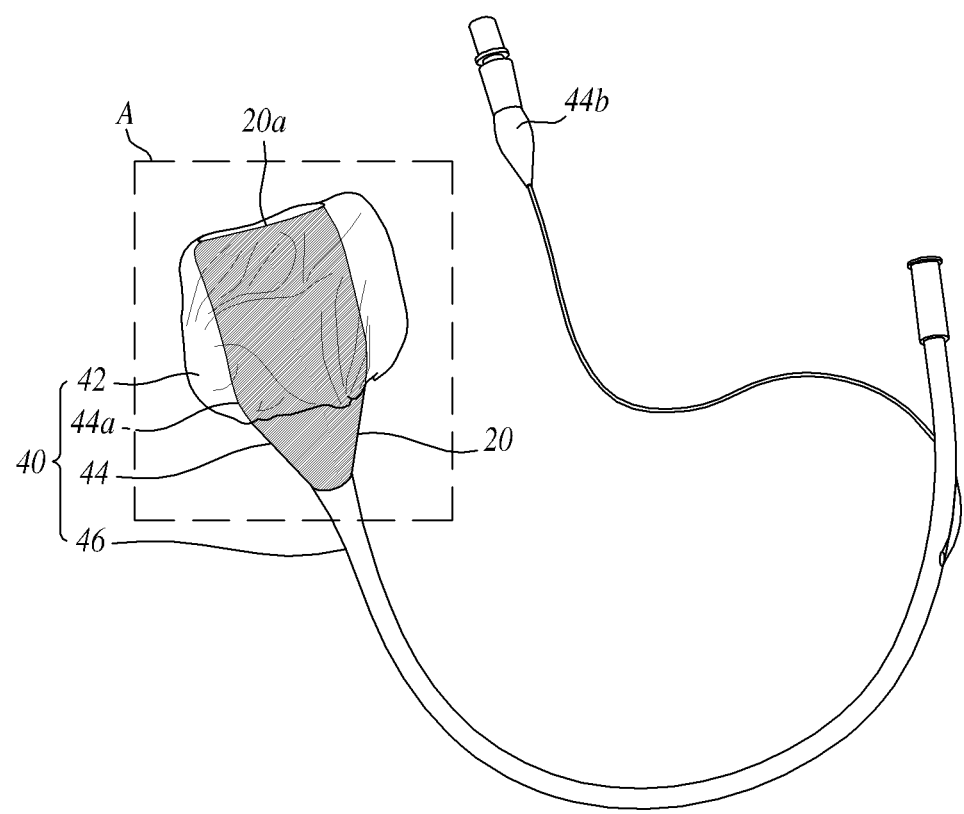
FIG. 2 is a view illustrating an amniotic fluid collector according to an embodiment of the present invention.
Figure 3:
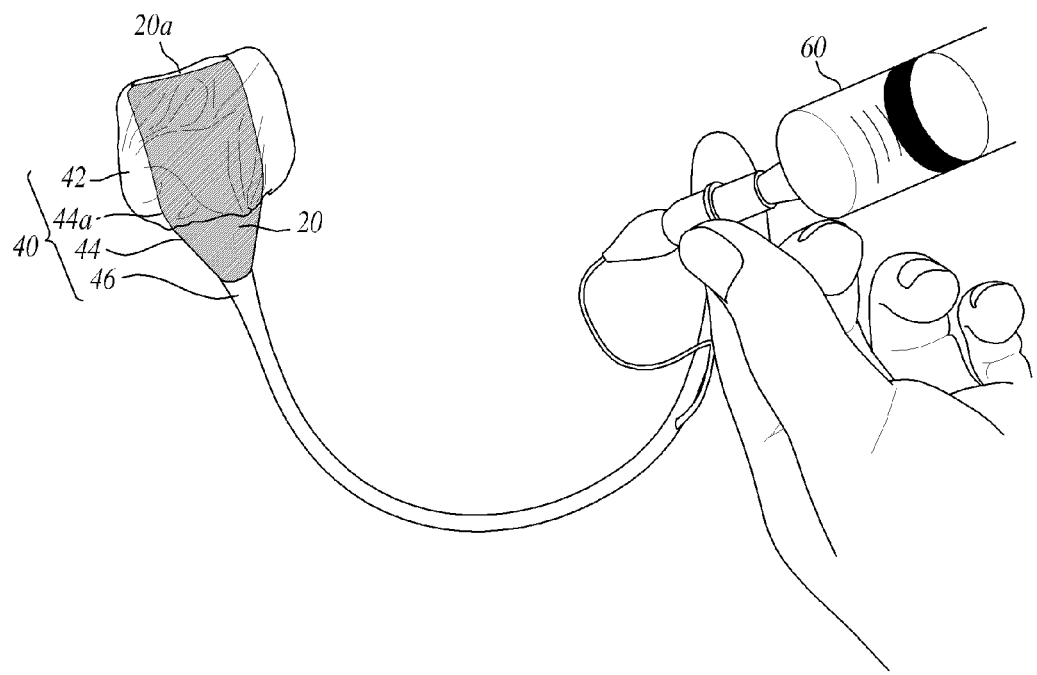
FIG. 3 is a view illustrating process of injecting an injection material to an expandable member of the amniotic fluid collector of FIG. 2.
Figure 4:
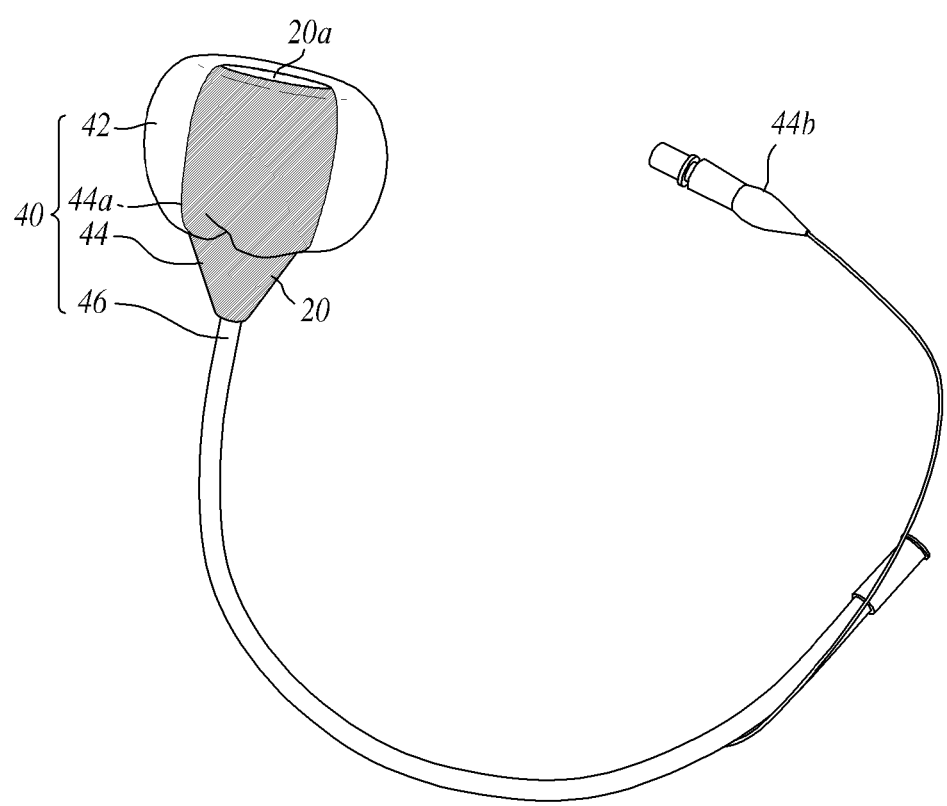
FIG. 4 is a view illustrating the expandable member of FIG. 2 in expanded state.

FIG. 2 is a view illustrating an amniotic fluid collector according to an embodiment of the present invention, FIG. 3 is a view illustrating process of injecting an injection material to an expandable member of the amniotic fluid collector of FIG. 2, FIG. 4 is a view illustrating the expandable member of FIG. 2 in expanded state, and FIG. 5 is an enlarged view of a portion A of FIG. 2.

Referring to the drawings, the amniotic fluid collector includes a receiving member 20 and a positioning portion 40 formed on the receiving member 20.

The receiving member 20 includes an aperture 20a formed on one side in a direction of insertion into the vagina of a pregnant woman 6 (FIG. 1), and a receiving compartment (not illustrated) formed therein to receive amniotic fluid.

Although not illustrated, the receiving compartment may be bored inward from the aperture 20a.

In detail, the receiving member 20 has a funnel shaped structure with a wide top and a narrow bottom in such a way that the top having the aperture 20a is widely spread to be in contact with an edge of a top of the vagina, that is, in contact with an edge of a bottom of the cervix, and the bottom is shaped to collect amniotic fluid gravitating down from above.

In addition, in the structure described above, the top is suitably sized horizontally for smooth insertion into the vagina and the bottom is smaller in size compared to the top, due to it being extended from the top.

Also, the positioning portion 40 includes an expandable member 42 to support the receiving member 20 in the vagina.

The expandable member 42 surrounds the receiving member 20, and expands upon injection of an injection material therein to securely urge against the inside of the vagina, thereby securely supporting the receiving member 20 in position.

That is, the expandable member 42 is formed along a side of the receiving member 20, and more preferably, the expandable member 42 is attached to outer circumferential surfaces of the top and the bottom, respectively. Accordingly, because the attached parts are separated from each other at a certain interval to provide a space formed between an outer surface of the receiving member 20 and an inner surface of the expandable member 42, into which the injection material is injected.

The expandable member 42 swells up gradually upon injection of the injection material therein, to thus securely urge against the inside of the vagina, and subsequently securely support the receiving member 20 in position without harming the inside of the vagina which is quite vulnerable.

The expandable member 42 may be formed from a material comprising silicone having elasticity and flexibility but not limited thereto. Any material with no harm to a human body and having elasticity and flexibility may be used.

In addition, the injection material may be a material including air or water.

The positioning portion 40 further includes a supplying tube 44 having one end 44a inserted into the expandable member 42 to be fluidly-connected to the expandable member 42 and the other end 44b through which the injection material is supplied.

That is, the supplying tube 44 has a configuration in which the one end 44a is connected to a bottom of the expandable member 42 in a manner in which an inner path of the supplying tube 44 is fluidly-connected to the inside of the expandable member 42.

In addition, when supplying the injection material, an injection material supplier such as a syringe 60 may be connected to the other end 44b of the supplying tube 44, thereby supplying the injection material.

The amniotic fluid collector may additionally include a grip tube 46 connected to the receiving member 20.

The grip tube 46 is connected to the receiving member 20 in such a way that the aperture 20a of the receiving member 20 is brought into close contact with the top of the vagina, and a withdrawal force is exerted to remove receiving member 20.

The grip tube 46 helps to position the receiving member 20 at a proper location to collect amniotic fluid, because a user can grip the grip tube 46 as well as the receiving member 20 conveniently in the process of inserting the receiving member 20 into the vagina in such a way that the insertion and positioning of the aperture 20a of the inserted receiving member 20 in close contact with the top of the vagina are enabled.

In addition, the grip tube 46 also facilitates removal of the receiving member 20 from the vagina, because the user can exert a withdrawing force on the grip tube 46 as well as the receiving member 20 with his or her hand.

The grip tube 46 may be formed from a material including natural rubber, urethane or plastic, with no harm to a human body, but not limited thereto. Any material with no harm to a human body and having properties similar to the material as described above, may be used.

In the grip tube 46, the supplying tube 44 is disposed longitudinally.

That is, the supplying tube 44 is formed in such a way that the one end 44a in the expandable member 42 is extended to be inserted into the grip tube 46 and the other end 44b is located outside through the grip tube 46.

In other words, because the supplying tube 44 is provided in an elongated arrangement in which the one end 44a is located in the expandable member 42 and the other end 44b is located outside, the arrangement is simplified and the connecting structure between the one end 44a of the supplying tube 44 and the expandable member 42 is stable.

Meanwhile, the receiving member 20 may be formed from a material including natural rubber, urethane or plastic, with no harm to a human body.

As described above, because the receiving member 20 is formed from a material harmless to a human body, and has a certain degree of elasticity externally, risk of causing injuries or harmful effects to a human body is prevented while amniotic fluid is collected.

In addition, the expandable member 42 may be formed from a material including silicone having elasticity and flexibility. The expandable member 42 is also formed from a material which is harmless to human body and which has freely varying volume.

Figure 6:
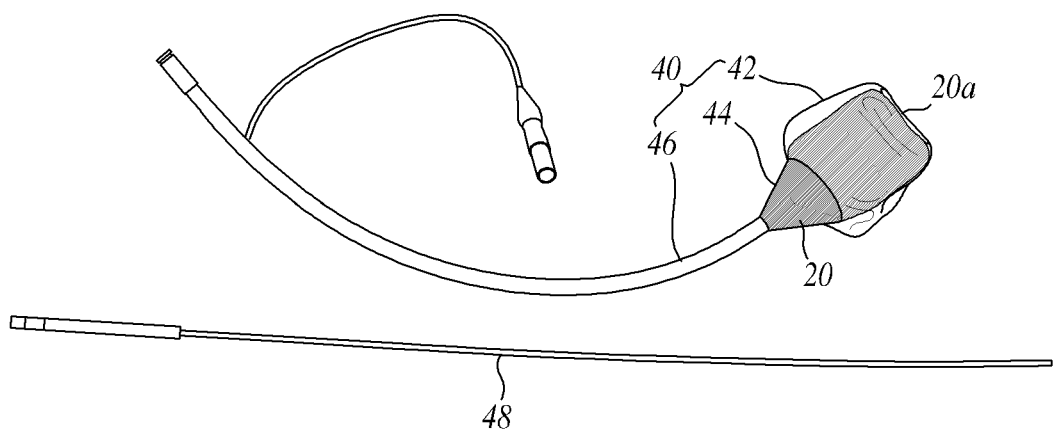
FIG. 6 is a view illustrating the amniotic fluid collector of FIG. 2 and a guide member.
Figure 7:
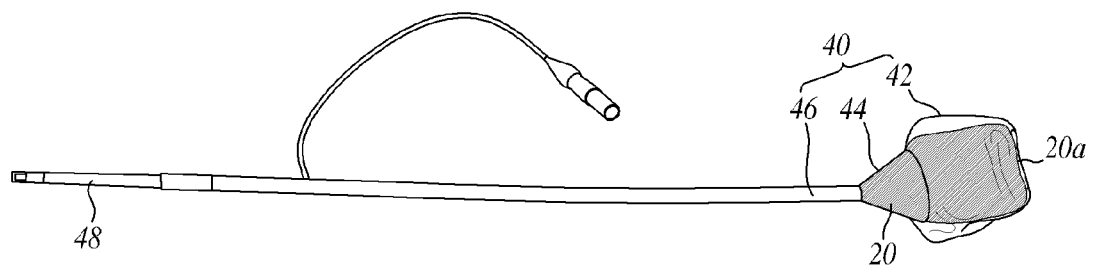
FIG. 7 is a view illustrating the guide member of FIG. 6, inserted into a grip tube.
Figure 8:
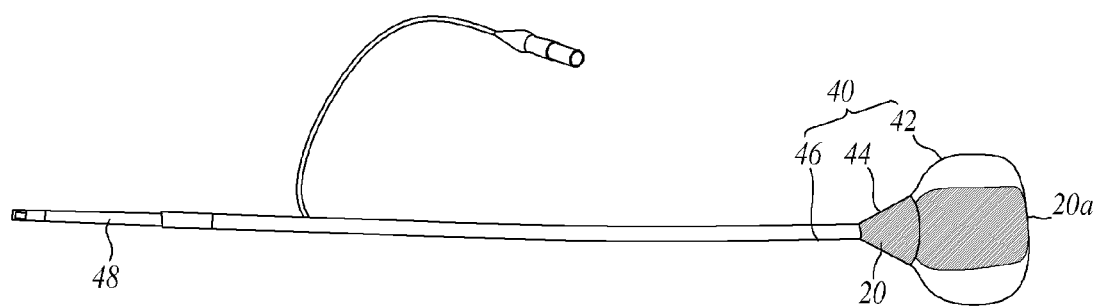
FIG. 8 is a view illustrating the expandable member in expanded state in the amniotic fluid collector of FIG. 7.
Figure 9:
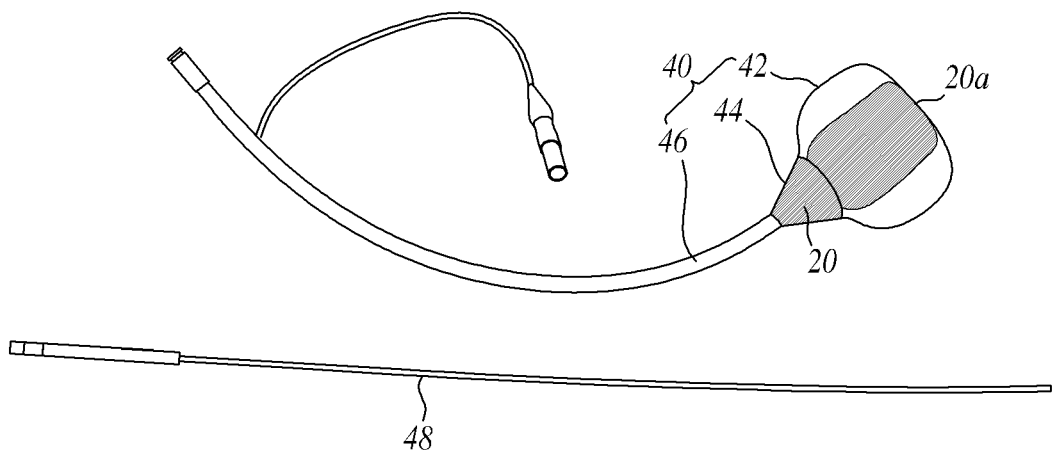
FIG. 9 is a view illustrating the guide member removed from the amniotic fluid collector of FIG. 8.

FIG. 6 is a view illustrating the amniotic fluid collector of FIG. 2 and a guide member, FIG. 7 is a view illustrating the guide member of FIG. 6, inserted into a grip tube, FIG. 8 is a view illustrating the expandable member in expanded state in the amniotic fluid collector of FIG. 7, and FIG. 9 is a view illustrating the guide member removed from the amniotic fluid collector of FIG. 8.

Referring to the drawings, the amniotic fluid collector may additionally include a guide member 48 with hardness, inserted in the grip tube 46, in order to exert an insertion force to insert the receiving member 20 into the vagina.

In detail, the guide member 48 is formed to be longer than the grip tube 46 in such a way that a part thereof is disposed outside when inserted into the grip tube 46 and has a certain degree of hardness not to be easily deformed by external pressure.

For example, the guide member 48 may be formed from a material comprising iron but not limited thereto. Any material with a certain degree of hardness may be used.

As a result, by using the amniotic fluid collector, which includes the receiving member 20 with the receiving compartment and the positioning portion 40 for positioning the receiving member 20 in the vagina, it is possible to conveniently and smoothly collect amniotic fluid from the uterus of the pregnant woman, while eliminating the pain and restlessness of a pregnant woman and a risk of complications.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An amniotic fluid collector comprising:
a receiving member comprising an aperture formed on only one side in a direction of insertion into the vagina of the pregnant woman, and a receiving compartment connected to the aperture to receive the amniotic fluid; and
a positioning portion for positioning the receiving member inside the vagina;
a grip tube connected to the receiving member to cause the aperture of the receiving member, inserted into the vagina, to be brought into a close contact with a top of the vagina and also to exert a withdrawal force to remove the receiving member from the vagina; and
a guide member with hardness to be inserted in the grip tube in order to apply an insertion force to insert the receiving member into the vagina,
wherein
the amniotic fluid collector is insertable into a vagina of a pregnant woman to collect amniotic fluid from a uterus of the pregnant woman;
the positioning portion comprises an expandable member which surrounds a top of a side surface of the receiving member and which is expandable upon injection of an injection material into the expandable member, to securely urge against an inner surface of the vagina and secure the receiving member in position; and
the receiving member has a funnel shaped structure, wherein the expandable member surrounds the funnel shaped structure and the top of the side surface of the receiving member.

2. The amniotic fluid collector of claim 1, wherein the receiving member is formed from a material comprising natural rubber, urethane or plastic, which is harmless to a human body.

3. The amniotic fluid collector of claim 1, wherein the expandable member is formed from a material comprising silicone with elasticity and flexibility.

4. The amniotic fluid collector of claim 1, wherein the injection material comprises air or water.

5. The amniotic fluid collector of claim 1, wherein the positioning portion further comprises a supplying tube having a first end inserted into the expandable member for fluid connection and a second end through which the injection material is supplied.

6. The amniotic fluid collector of claim 5, wherein the supplying tube is formed in such a way that the first end, inserted in the expandable member, is extended to be inserted into the grip tube, and the second end is located outside the grip tube.

7. The amniotic fluid collector of claim 1, wherein the grip tube is formed from a material comprising natural rubber, urethane or plastic, which has no harm to a human body.

8. The amniotic fluid collector of claim 1, wherein the guide member is formed from a material comprising iron.

* * * * *